United States Patent [19]

Tanzi et al.

[11] Patent Number: 5,606,012
[45] Date of Patent: *Feb. 25, 1997

[54] POLYETHERAMIDOAMINE HYDROGELS AS HEPARINIZABLE MATERIALS

[75] Inventors: Maria C. Tanzi, Milan; Gianfranco Palumbo, Pescara, both of Italy

[73] Assignee: Societa' Consortile Ricerche Angelini S.p.A., Pescara, Italy

[ * ] Notice: The term of this patent shall not extend beyond the expiration date of Pat. No. 5,571,890.

[21] Appl. No.: 331,512

[22] PCT Filed: Apr. 16, 1993

[86] PCT No.: PCT/EP93/00920

§ 371 Date: Nov. 22, 1994

§ 102(e) Date: Nov. 22, 1994

[87] PCT Pub. No.: WO93/21257

PCT Pub. Date: Oct. 28, 1993

[30] Foreign Application Priority Data

Apr. 21, 1992 [IT] Italy .................................. MI92A0955

[51] Int. Cl.⁶ ...................................................... C08G 73/02
[52] U.S. Cl. ........................... 528/342; 528/170; 528/176; 528/183; 528/184; 528/186; 528/192; 528/194; 528/195; 528/208; 528/220; 528/224; 528/228; 528/229; 528/310; 528/322; 528/328; 528/332; 528/345
[58] Field of Search ..................... 528/183, 184, 528/186, 310, 322, 170, 176, 192, 194, 195, 208, 220, 224, 228, 229, 342, 345, 328, 332

[56] References Cited

FOREIGN PATENT DOCUMENTS 3721057   1/1989   Germany .
WO9321256 10/1993   WIPO .

OTHER PUBLICATIONS

Chemical Abstracts, vol. 114, No. 14, 8 Apr. 1991, Abstract No. 123814y, Penczek, et al, "Preparation of cross–linked hydrogels", p. 51. col. 1.

Journal of Applied Polymer Science, vol. 28, 1983, pp. 3361–3368, Pesavento, et al, "Applied Macroinorganics. IV. Effects of the Crosslinking Agent on Protonation, and Metal Ions Complexing Abilities, of Ion Exchange Resins with Poly(amido–Amine) Structure" The month of publication is not available.

Biomaterials, vol. 5, Nov. 1984, pp. 357–361, Tanzi, et al., "Synthesis and characterisation of poly(amido–amines)s belonging to two different homologous series".

Chemical Abstracts, vol. 106, No. 26, 29 Jun. 1987, Abstract No. 214758j, Kopylova, et al, "Structure and properties of cross–linked hydrogels based on a poly(acylic acid)–polyethyleneimine polyelectrolyte complex", p. 26, col. 2.

Primary Examiner—James J. Seidleck
Assistant Examiner—P. Hampton-Hightower
Attorney, Agent, or Firm—Griffin, Butler, Whisenhunt & Kurtossy

[57] ABSTRACT

Polymeric polyetheramidoamine hydrogel materials, which are capable of complexing heparin in physiological conditions are herein described. Said materials are useful in the manufacturing of medical devices.

12 Claims, No Drawings

POLYETHERAMIDOAMINE HYDROGELS AS HEPARINIZABLE MATERIALS

The present invention relates to polyetheramidoamine hydrogels, to processes for the preparation thereof and to the use thereof as heparin adsorbing materials.

BACKGROUND OF THE INVENTION

In the biomedical field, the development of thromboresistant materials is hindered by the interaction of the blood itself with artificial surfaces. In normal situations, platelets or blood components do not adhere to the vasal lumen, whereas the contact with a synthetic material causes platelet deposition, often together with thrombotic phenomena. Accordingly, polymeric surfaces, which show the ability of inhibiting the formation of thrombus, are of great interest for the preparation of cardiovascular protheses and devices to be used in contact with blood.

Antithrombogenic surfaces can be divided into three main classes:
I) Surfaces promoting the formation of neointima, since they have adhesive properties for endothelial cells. Antithrombogenicity is due to the functional capacity of the cells themselves.
II) Surfaces capable of blocking the thrombus formation, therefore inhibiting:
   a) platelet aggregation or activation; b) fibrin network formation.
III) Thrombolytic surfaces.

Surfaces belonging to the second class are particularly important from a technological point of view, and the present invention refers to this field.

Antithrombogenic materials must have one or more of the following requirements:
1. Low critical surface tension;
2. Negative surface charge;
3. Hydrated polymeric surface at the interface with blood;
4. Heparin binding capability, either by covalent or ionic bond, or heparin controlled release capability.
5. Capability of selectively adsorbing "passivant" blood proteins, such as albumin, or of interacting with blood elements (endothelial cells) without activating coagulation processes.

PRIOR ART

The surfaces capable of blocking thrombogenic process are mainly represented by the so called heparinized surfaces, namely those materials which interact with the heparin molecule such as to ensure its natural anticlotting activity. The antithrombotic effect can be obtained either by binding heparin stably to the material surface, thus acting mainly in the circulatory site where said material resides, for example a heart valve, or by means of a controlled release of heparin from the material itself, but without a complete release of heparin from the graft.

Hydrogels are three-dimensional lattices made of hydrophilic polymers or copolymers, which are capable of swelling in water or biological fluids. In the biomedical field, hydrogels are grouped into neutral, ionic or with interpenetrated lattices.

Hydrogels can absorb high percentages of water and show a low interfacial free energy in the aqueous systems, which renders them excellent materials to be used in contact with blood.

Polymers having a polyamidoamine structure (PAA) are well known as heparin complexing agents. (Ferruti e Al.; Polymer, 26, (1985), 133; Tanzi e Al.; Biomaterials, 5, (1984), 357). The formation of stable heparin complexes is due to the strong ionic interaction between the negative charges of heparin and the tertiary amino groups of the PAA chains, which are protonated at physiological pH, together with electrostatic interactions between the two types of macromolecules.

The application of the PAA in the haemocompatible field is difficult as none of the known PAA possesses suitable mechanical characteristics. Consequently, these polymers have been grafted or copolymerized with other polymeric structures, as to obtain suitable elastomeric materials having the desired properties (Barbucci e Al.; Biomaterials, 10, (1989) 299–308, Tanzi, Levi; J. of Biomed. Mater. Res. 23; (1989) 863).

Crosslinked PAA were described by Ferruti e Al. in Polymer, 26, (1985), 133, as heparin sequestering filters, but said structures are insufficiently hydrophilic and elastic.

DESCRIPTION OF THE INVENTION

It has now been found that hydrophilic crosslinked polyetheramidoamine polymers have surprisingly shown haemocompatible heparin-adsorbing properties, which have improved hydrophilic and elastic characteristics with respect to the crosslinked polyamidoamine of the above cited prior art.

Hydrogels of the invention are formed by polymeric polyetheramidoamine and/or polyamidoamine chains ending with acryl groups, hereinafter named as "prepolymers", in their turn crosslinked with suitable crosslinking agents.

The prepolymers are obtained by a Michael's like nucleophilic polyaddition, starting from bisacrylamido bifunctional monomers named [AA], of formula (I),

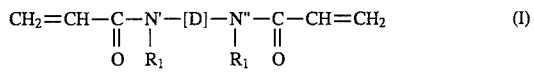

wherein:
$R_1$ is hydrogen;
[D] is $C_1$–$C_{12}$ straight or branched alkylene unsubstituted or substituted with one or more hydroxy groups, optionally interrupted by oxygen atoms, or [D], together with N' and N", forms a piperazine ring, in which case $R_1$ is absent;
which are reacted with α-ω-diamino bifunctional monomers, named [BB], of formula (II):

wherein:
$R_2$ is $C_1$–$C_{10}$ straight or branched alkyl, optionally substituted with one or more hydroxy groups;
[E] is $C_1$–$C_{12}$ straight or branched alkylene unsubstituted or substituted with one or more hydroxy groups, optionally interrupted by oxygen atoms;
or the monomers [AA] are reacted with monofunctional monomers, named [B], of formula (IIa):

wherein [F] has the same meanings as [E] and it can also be interrupted by tertiary amino groups. Preferred alkylene groups [D] are included in the following formula (III):

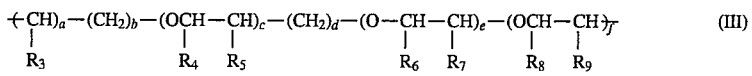 (III)

wherein a, b, c, d, e and f are numbers 0 to 12, $R_3$ is methyl, hydroxy, $C_1$–$C_{12}$ alkyl, optionally substituted with one or more hydroxy groups;

$R_4$–$R_9$ are independently hydrogen or methyl.

Particularly preferred alkylene groups [D] are those which, together with the nitrogen atoms N' and N", form the polyoxyalkylenediamines known under the commercial name Jeffamine®, manufactured by Texaco Chemical Company.

Even more preferred monomers are monomers [AA], in which [D] is a group of formula (III) wherein $R_3$ is methyl, $R_4$ is hydrogen, $R_5$ is methyl, a and b are 1, c is an integer 2 to 12 included, d, e, f are 0; or:

$R_3$, $R_4$ and $R_9$ are methyl, $R_5$–$R_8$ are hydrogen, a and b are 1, c is about 8.5, d is 0, the sum e+f is about 2.4; or:

a, d, f are 0, b is 2, c and e are 1, $R_4$–$R_7$ are hydrogen. Particularly preferred are bisacryloylpiperazine (BAP), methylene-bis-acrylamide (BAC), dihydroxyethylenebisacrylamide (DHEBA).

Particularly preferred compounds of formula (II) are those in which $R_2$ are both 2-hydroxypropyl, [E] has the following formula:

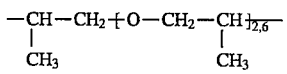

In some particular cases monofunctional monomer (IIa) are used as chain extending agents between two monomers [AA].

The resulting prepolymer has the following formulae:

or

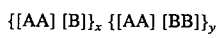

wherein x and y are numbers comprised between 1 and 50 selected to have prepolymers with a maximum molecular weight Mw 20,000.

The cross-linking of the resulting prepolymer can take place through two reaction mechanisms: a) by Michael nucleophilic polyaddition; b) radicalically.

In the case of cross-linking by nucleophilic polyaddition, at least tetrafunctional crosslinking agents are used, of formula (IV):

$$H_2N-[G]-NH_2 \quad (IV)$$

wherein:

[G] is $C_2$–$C_{12}$ straight or branched alkylene, unsubstituted or substituted with one or more hydroxy groups, optionally interrupted by oxygen atoms and/or >$NR_{10}$ amino groups, wherein $R_{10}$ is hydrogen or $C_1$–$C_4$ alkyl.

Preferred compounds are those of formula (IV), wherein [G] represents the polyoxyalkylene residues comprising Jeffamine® of the M, D, ED, C-346, DU, EDR-148 and T series, described in the publication by Texaco Chemical Company "The JEFFAMINE® Polyoxyalkyleneamines", 1987.

The stoichiometric ratio, considered in equivalents, of the monomer [AA] to the sum of the monomer [BB] with the crosslinking agent must be such as to the number of acryl bonds on [AA] be the same as the number of the hydrogen atoms bound to the amino nitrogen atoms, i.e., each molecule [AA] corresponds to one molecule [BB] and to half a molecule of the crosslinking agent.

In case cross-linking is carried out radicalically, monomers with unsaturated end groups such as [AA], or bisacrylates, bismetacrylates or diallyl compounds can be used.

Examples of said crosslinking agents are ethylene glycol dimetacrylate, diallyltartardiamide.

Cross-linking by Michael nucleophilic polyaddition can be carried out according to two different methods.

a) in two steps, first preparing the prepolymer {[AA] [BB]}$_x$, which, optionally after recovering it, is reacted with the crosslinking agent;

b) in a single step, wherein the monomers and the crosslinking agent/s are reacted simultaneously.

The reaction medium consists of a polar solvent or a mixture of polar solvents, such as water or water-miscible alcohols. The reaction temperature ranges from 0° to 60° C., preferably from 20° to 40° C.

The radicalic reaction can be carried out in aqueous or water-alcohol solvents, with radical promoters, such as ammonium persulfate, at a temperature from 20° to 40° C. Otherwise, the reaction can be carried out in organic solvents with radical promoters, such as organic peroxides, dibenzoyl-peroxide and azobisisobutyronitrile, at a temperature higher than 60° C.

The hydrogel will have different cross-linking degrees, depending on the desired physical characteristics.

The final product will be elastic and have a swelling capability in water from 50 to 500%.

The following examples further illustrate the invention.

EXAMPLE 1

Hydrogel dimethylhexanediamine/methylene-bis-acrylamide/Jeffamine EDR-148 (DA1/2 JR)

1.65 g (11.44 mmoles) of dimethylhexanediamine (DMESA) were reacted with 2.11 g (9.8 mmoles) of methylene-bis-acrylamide (BAC), in 10 ml of distilled water at room temperature. The mixture was left to react for 3 days shielding from light, to give a polyamidoamine prepolymer, mainly ending with vinyl groups. After that, the prepolymer was cross-linked directly by adding the reaction mixture with 170 mg (1.144 mmoles) of Jeffamine EDR-148. The reaction was carried out for 3 days at room temperature. When the reaction was over, the product was repeatedly washed with water and methanol to remove the unreacted compounds. An elastic opaque white gel was obtained (89% yield).

EXAMPLE 2

Preparation of the Hydrogel through Recovering of the Polymer (DA1/2+JR)

2 g (13.86 mmoles) of DMESA were dropped into a solution containing 2.56 g (16.60 mmoles) of BAC in 12 ml of distilled water and left to react at room temperature for 3 days. After the reaction, the prepolymer was recovered by evaporation of the solvent under vacuum at 30° C.

The dried product was dissolved in $CHCl_3$ (1 g/5 ml $CHCl_3$) and the solution was dropped into 300 ml of ethyl ether under magnetic stirring. The precipitate was washed twice with ethyl ether, filtered and dried.

The control with HPLC (eluent buffer phosphate, pH 6.8; Bio-gel TSK20 and TSK40 columns) and with TLC ($CHCl_3$: MeOH 95:5, developer $K_2CO_3$—$KMnO_4$) evidenced the absence of unreacted starting products.

The structure of the prepolymer was confirmed by NMR analysis.

The prepolymer was dissolved in water to obtain a 20% w/v solution. Subsequently 57 mg (13.86 mmoles) of Jeffamine EDR-148 were added and the cross-linking reaction was carried out for 3 days at room temperature. The product was recovered as in Example 1, to obtain a transparent elastic gel (96% yield).

EXAMPLE 3

Dimethylhexanediamine/methylene bisacrylamide/Jeffamine EDR 148 Hydrogel (DA1/4JR)

With a process similar to the one described in Example 1, and using 1.01 g (7 mmoles) of DMESA, 1.51 g (9.8 mmoles) of BAC in 8 ml of distilled water and subsequently 207 mg of EDR 148, a transparent elastic gel was obtained (84% yield).

EXAMPLE 4

Dimethylhexanediamine/methylene-bisacrylamide/ ethylenediamine hydrogel (DAI/2ED)

A gel was prepared for comparison purposes, starting from the prepolymer of Example 1, which was cross-linked with 69 mg (1.144 mmoles) of ethylenediamine, according to the procedure de scribed in U.S. Pat. No. 3,865,723. A brittle opaque gel was obtained (69% yield).

EXAMPLE 5

Jeffamine C346/bisacryloylpiperazine/Jeffamine D-2000 Hydrogel (JAJd 2000)

3.57 g (10.32 mmoles) of Jeffamine C346, 4 g (20,64 mmoles) of BAP in 10 ml of distilled water were reacted, according to the method described in Example 1, for 4 days, shielding from light and at room temperature. At the end of the reaction, 10.31 g (5.16 mmoles) of Jeffamine D 2000 and 15 ml of methanol were added. The cross-linking reaction was carried out for 7 days at room temperature. An elastic light yellow gel was obtained, which was washed with water and methanol to remove the unreacted products (70% yield).

EXAMPLE 6

Hydrogel from prepolymer [Jeffamine C346/BAP], cross-linked with BAP (JB1Az)

1.8 g (5.2 mmoles) of Jeffamine C346 in 2 ml of distilled water were treated with 1.11 g (5.72 mmoles) of BAP. The reaction was carried out for 2 days at room temperature and shielding from light. At the end of the reaction, the mixture was deareated under vacuum and nitrogen was introduced. After that, 60 mg of radicalic promoter azobisisobutyronitrile, suspended in 15 ml of water were added. The cross-linking was carried out at 60° C. for 3 hours. A brittle light yellow gel was obtained (60% yield).

EXAMPLE 7

Hydrogel from prepolymer [Jeffamine C346/BAP] cross-linked with BAP (JB3Az)

With a process similar to that described in Example 6, 1.66 g (4.79 mmoles) of Jeffamine C346 and 1.21 g (6.23 mmoles) of BAP were reacted in 2 ml of distilled water. A brittle light yellow gel was obtained (63% yield).

EXAMPLE 8

Hydrogel from prepolymer [Jeffamine C346/BAP] cross-linked with BAP (JB3Az)

The procedure of the Example 7 was repeated and the amount of unreacted BAP was analyzed by HPLC, which amount corresponded to about 9% w/w compared with the starting amount, then the reaction mixture was added with 0.292 g of BAP (10% by weight on Jeffamine C346), nitrogen was repeatedly removed and bubbled therein and 5 ml of a 5% w/w ammonium persulfate solution were added. Cross-linking took place immediately: the white opaque gel was washed with distilled water and repeatedly with methanol (93% yield).

EXAMPLE 9

Hydrogel from prepolymer [Jeffamine c346/BAP] crosslinked with BAC (JC 10 Aps)

With a procedure similar to the one of the Example 8, except BAC (1.56 g at the beginning of crosslinking and further 0.292 g after 8 days) was used. At the end of the $8^{th}$ day, unreacted BAC was about 9% (83% Yield).

The gel prepared as described in the above examples were tested for heparin adsorption and release by means of the PTT test (clotting test).

The tests were carried out on the gels obtained in the Examples 1 and 2, namely DA1/2JR and DA1/2+JR, respectively, and on the gels obtained in the Examples 3, 4 and 5, namely DA1/4JR, DA1/2ED and JAJd. The samples were heparinized according to the procedure described in Tanzi, Levi, J. of Biomed. Mater. Res. 23 (1989), 863. The samples were immersed in heparin sodium salt solutions, 150.000 IU/g (Sarsyntex) having 0.1% and 1% concentrations in acetate (AB, pH 4.8) or phosphate (PBS, pH 7.4) buffers. Immersion lasted 16 hours, then the samples were extracted and twice washed with distilled water.

The treatment with 1% heparin (see Table 1, n.1) was the well known one in the case of the polyamidoamines. The treatment with 0.1% heparin (see Table 1, n.4 and 5) was carried out in order to evaluate if the whole heparin could be completely adsorbed from a diluted solution. The treatment with heparin in PBS (Table 1, n.3) was intended to verify heparin absorption at physiological pH.

The evaluation of heparin release in PBS was carried out by stirring the eparinized samples for several intervals, until heparin disappeared from eluates, each interval was 30 minutes long.

The evaluation of heparin release in NaOH solution was carried out by immersing the same sample in 0.1N NaOH solution, until heparin disappeared from eluates.

In this way, "weakly" adsorbed heparin, i.e. by means of electrostatic interactions, was released and could be evaluated in PBS, whereas more stably adsorbed heparin, i.e. by means of strong ionic interaction, was released only after treatment with NaOH (wherein tertiary nitrogen atoms deprotonate).

Heparin amount was calculated with aPTT test (activated Partial Thromboplastin Time), with an Elvi Logos Digiclot coagulometer and Logos reagents, by additions of 50 µl of bovine serum to 50 µl of both known and unknown solutions.

Two calibrations curves were considered: the one with PBS and the other with 0.1N NaOH (neutralized with HCl and containing a final NaCl concentration of 0.9%). The results are shown in the following Table 1.

TABLE 1

Heparin adsorption. aPTT test: evaluation of heparin release from heparinized samples, both in physiological (PBS; pH 7.4) and alkaline (0.1 N NaOH) conditions.

| Sample | Heparinization | Residue heparin in solution (mg) | Released heparin | |
|---|---|---|---|---|
| | | | PBS (mg) | NaOH (mg) |
| 1.) DA1/2JR | 1% Hep. in AB overnight (tot. 30 mg) | ~7 g | 0.26 (<<1%) | 16 (53%) |
| 2.) DA1/2JR (*) | 0% Hep. in AB overnight | | 0.0017 | |
| 3.) DA1/2JR | 1% Hep. in PBS overnight (tot. 20 mg) | 0.180 g | 0.236 (1.2%) | 19 (95%) |
| 4.) DA1/2JR | 0.1% Hep. in AB overnight (tot. 3 mg) | 0.22 g | 0.044 (1.5%) | 2.8 (93%) |
| 5.) DA1/2+JR | 0.1% Hep. in AB overnight (tot. 3 mg) | 0.015 g | 0.0805 (2.7%) | 2.7 (90%) |
| 6.) DA1/2ED (**) | 0.1% Hep. in AB overnight (tot. 2 mg) | 34 µg | 0.100 | (>0.100) |
| 7.) DA1/4 JR | 1% Hep. in AB (tot. 30 mg) | | 0.443 (<1%) | 13.5 (45%) |
| 8.) JAJd | 1% Hep. in AB (tot. 200 mg) | | 3.22 (1.6%) | 167.5 (83.5%) |

AB = acetate buffer ( pH = 4.6)
PBS = phosphate buffer
(*) = blank for the heparinization procedure
(**) = non homogeneous gel, highly swollen in acetate buffer.

The obtained results confirm these gels are interesting as potential materials sequestering heparin even from solutions having physiological pH, and also as heparinizing materials for coating the surfaces of devices or protheses to be contacted with blood.

In the above Table, points 1 to 4 show the results of the heparinization of the gels obtained without isolating the prepolymer. It can be seen that heparin remains adsorbed not only after acid buffer treatment (AB), but also after physiological pH treatment (PBS, pH =7.4). Heparin, which is initially present in the solution is completely adsorbed, both in 1% and in 0.1% one. The release occurs partly in PBS, but mostly in alkaline conditions (0.1N NaOH). The data obtained by using a gel prepared from a previously isolated prepolymer (point 5) confirm the ones obtained with the previous gel, which was prepared without isolating the prepolymer. In the comparison with a product, which was crosslinked with other than Jeffamine, but with a diamine like ethylenediamine (described in U.S. Pat. No. 3,865,723), it should be noticed that the gel is not homogeneous, is poorly stable and reliable data may not be obtained (see Table 1, n.6).

We claim:

1. Polyetheramidoamine hydrogels consisting of polyetheramidoamine and/or polyamidoamine prepolymers of molecular weight Mw not higher than 20,000, cross-linked by Michael nucleophilic polyaddition with α-ω-diamino monomers or oligomers, said hydrogels having a swelling degree in water from 50 to 500%.

2. Polyetheramidoamine hydrogels consisting of polyetheramidoamine and/or polyamidoamine prepolymers of molecular weight Mw not higher than 20,000, cross-linked by radicalic polyaddition with bisacrylamide, bisacrylate, bismetacrylate or diallyl monomers or oligomers, said hydrogels having a swelling degree in water from 50 to 500%.

3. Hydrogels according to claim 1, wherein the prepolymers have the formulae:

$\{[AA] [BB]\}_x$ or

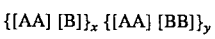

$\{[AA] [B]\}_x \{[AA] [BB]\}_y$ wherein x and y are numbers comprised between 1 and 50, selected so that the prepolymer has a molecular weight Mw not higher than 20,000, wherein:

[AA] is a compound of formula (I):

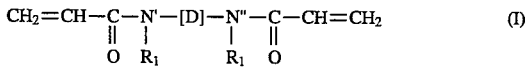

$$CH_2=CH-\underset{O}{\overset{\|}{C}}-\underset{R_1}{\overset{|}{N'}}-[D]-\underset{R_1}{\overset{|}{N''}}-\underset{O}{\overset{\|}{C}}-CH=CH_2 \qquad (I)$$

wherein:

R$_1$ is hydrogen;

[D] is C$_1$–C$_{12}$ straight or branched alkylene unsubstituted or substituted with one or more hydroxy groups, optionally interrupted by oxygen atoms, or [D], together with N' and N", forms a piperazine ring, in which case R$_1$ is absent;

[BB] is a compound of formula (II):

$$HN-[E]-NH \atop \phantom{HN-}R_2 \phantom{-[E]-}R_2 \qquad (II)$$

wherein:

R$_2$ is C$_1$–C$_{10}$ straight or branched alkyl, optionally substituted with one or more hydroxy groups;

[E] is C$_1$–C$_{12}$ straight or branched alkylene unsubstituted or substituted with one or more hydroxy groups, optionally interrupted by oxygen atoms;

[B] is a compound of formula (IIa):

$$H_2N-[F]-H \qquad (IIa)$$

wherein [F] has the same meanings as [E] and it can also be interrupted by tertiary amino groups.

4. Hydrogels according to claim 3, wherein [D] is a group of formula (III):

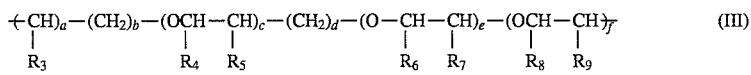

wherein
- a, b, c, d, e and f are numbers 0 to 12, $R_3$ is methyl, hydroxy, $C_1$–$C_{12}$ alkyl, optionally substituted with one or more hydroxy groups;
- $R_4$–$R_9$ are independently hydrogen or methyl.

5. Hydrogels according to claim 3, wherein bisacrylamides [AA] are selected from the group consisting of bisacryloylpiperazine, methylene-bis-acrylamide, dihydroxyethylenebisacrylamide, and bisacrylamides wherein the group [D], together with the nitrogen atoms N' and N", forms the following Jeffamines®: EDR-148, D-230, D-400, ED-600.

6. Hydrogels according to claim 3, wherein compound [BB] is the Jeffamine® C346 of formula:

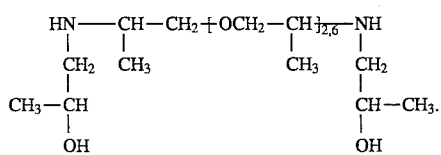

7. Hydrogels according to claim 1 wherein the prepolymers are cross-linked with compounds of formula (IV):

wherein:
- [G] is $C_2$–$C_{12}$ straight or branched alkylene, unsubstituted or substituted with one or more hydroxy groups, optionally interrupted by oxygen atoms and/or >$NR_{10}$ amino groups, wherein $R_{10}$ is hydrogen or $C_1$–$C_4$ alkyl.

8. Hydrogels according to claim 7 wherein the prepolymers are cross-linked with compounds of formula (IV) wherein [G] represents the polyoxyalkylene residues comprising Jeffamines® of the M, D, ED, C-346, DU, EDR-148 and T series.

9. A process for the preparation of hydrogels of claim 3, which comprises cross-linking the prepolymers of formula $\{[AA]\ [BB]\}_x$ or $\{[AA]\ [BB]\}_x\ \{[AA]\ [BB]\}_y$, wherein [AA], [BB], x and y have the above meanings, with crosslinking agents of formula (IV)

wherein [G] is $C_2$–$C_{12}$ straight or branched alkylene, unsubstituted or substituted with one or more hydroxy groups, optionally interrupted by oxygen atoms and/or >$NR_{10}$ amino groups, wherein $R_{10}$ is hydrogen or $C_1$–$C_4$ alkyl, through a nucleophilic polyaddition mechanism, in a polar solvent, at a temperature from 20° to 40° C., and shielded from light.

10. A process for the preparation of the hydrogels of claim 3, which comprises cross-linking the prepolymers of formula $\{[AA]\ [BB]\}_x$ or $\{[AA]\ [B]\}_x\ \{[AA]\ [BB]\}_y$, wherein [AA], [BB], [B], x and y have the meanings above, with [AA] crosslinking agents or with bisacrylate, bismetacrylate or diallyl crosslinking agents, through a radicalic polyaddition mechanism, in the presence of a radical promoter in an aqueous or inert organic solvent, at a temperature from 20° to 80° C., and shielded from light.

11. Heparinizable compositions containing the hydrogels of claim 1.

12. Hydrogels-heparin complexes, wherein the hydrogels are the polyetheramidoamine polymers of claim 1.

* * * * *